United States Patent
Avery et al.

(10) Patent No.: US 10,207,056 B2
(45) Date of Patent: Feb. 19, 2019

(54) SET OF MEMBERS FOR A DRUG DELIVERY DEVICE, DRUG DELIVERY DEVICE AND SET OF DRUG DELIVERY DEVICES

(75) Inventors: Richard James Vincent Avery, Gloucestershire (GB); Christopher Nigel Langley, Warwickshire (GB); James Alexander Senior, Warwickshire (GB); James Alexander Davies, Warwickshire (GB)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 159 days.

(21) Appl. No.: 13/582,561

(22) PCT Filed: Mar. 30, 2011

(86) PCT No.: PCT/EP2011/054876
§ 371 (c)(1),
(2), (4) Date: Dec. 4, 2012

(87) PCT Pub. No.: WO2011/121003
PCT Pub. Date: Oct. 6, 2011

(65) Prior Publication Data
US 2013/0072879 A1 Mar. 21, 2013

(30) Foreign Application Priority Data
Mar. 31, 2010 (EP) .................................. 10158674

(51) Int. Cl.
*A61M 5/31* (2006.01)
*A61M 5/00* (2006.01)
(Continued)

(52) U.S. Cl.
CPC .......... *A61M 5/3129* (2013.01); *A61M 5/003* (2013.01); *A61M 5/24* (2013.01);
(Continued)

(58) Field of Classification Search
CPC ...... A61M 5/002; A61M 2205/582–2205/583; A61M 2205/58
(Continued)

(56) References Cited

U.S. PATENT DOCUMENTS

| 533,575 A | 2/1895 | Wilkens |
| 2,505,411 A * | 4/1950 | Kolodny ............. A61M 5/3129 604/207 |

(Continued)

FOREIGN PATENT DOCUMENTS

| EP | 0937471 | 8/1999 |
| EP | 0937476 | 8/1999 |

(Continued)

OTHER PUBLICATIONS

International Preliminary Report on Patentability for Int. App. No. PCT/EP2011/054876, dated Jun. 13, 2012.
(Continued)

*Primary Examiner* — Edelmira Bosques
(74) *Attorney, Agent, or Firm* — Fish & Richardson P.C.

(57) ABSTRACT

A set of members for a drug delivery device comprises at least two components for the device, wherein both components are provided with a marking, the markings being substantially equivalent or identical. Furthermore, a drug delivery device and a set of drug delivery devices are provided.

14 Claims, 5 Drawing Sheets

(51) Int. Cl.
*A61M 5/24* (2006.01)
*A61M 5/20* (2006.01)
*A61M 5/315* (2006.01)
*A61M 5/32* (2006.01)

(52) U.S. Cl.
CPC .......... *A61M 5/20* (2013.01); *A61M 5/31525* (2013.01); *A61M 5/31551* (2013.01); *A61M 5/3202* (2013.01); *A61M 2005/2488* (2013.01); *A61M 2205/582* (2013.01); *A61M 2205/584* (2013.01); *A61M 2205/6036* (2013.01); *A61M 2205/6045* (2013.01); *A61M 2205/6081* (2013.01)

(58) Field of Classification Search
USPC .................................................. 604/189, 187
See application file for complete search history.

(56) References Cited

U.S. PATENT DOCUMENTS

| | | | |
|---|---|---|---|
| 2,706,464 A * | 4/1955 | North ............... | A61J 7/04 116/308 |
| 4,610,666 A | 9/1986 | Pizzino | |
| 4,919,657 A * | 4/1990 | Haber et al. ............. | 604/232 |
| 4,921,277 A * | 5/1990 | McDonough ............ | 283/81 |
| 5,102,169 A * | 4/1992 | Mayfield ............... | 283/115 |
| 5,103,978 A * | 4/1992 | Secor ............... | G11B 23/40 206/308.3 |
| 5,226,895 A | 7/1993 | Harris | |
| 5,279,586 A * | 1/1994 | Balkwill ............ | A61M 5/3158 222/309 |
| 5,304,152 A | 4/1994 | Sams | |
| 5,320,609 A | 6/1994 | Haber et al. | |
| 5,376,081 A * | 12/1994 | Sapienza ............... | 604/207 |
| 5,383,865 A | 1/1995 | Michel | |
| 5,423,752 A * | 6/1995 | Haber et al. ............ | 604/86 |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,645,534 A * | 7/1997 | Chanoch ............... | 604/189 |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,227,371 B1 * | 5/2001 | Song ............... | G09B 21/003 206/534 |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 7,291,132 B2 * | 11/2007 | DeRuntz et al. ............. | 604/207 |
| 2002/0017784 A1 * | 2/2002 | Merry et al. ............... | 283/81 |
| 2002/0052578 A1 | 5/2002 | Moller | |
| 2002/0120235 A1 | 8/2002 | Enggaard | |
| 2003/0050609 A1 | 3/2003 | Sams | |
| 2004/0024365 A1 * | 2/2004 | Bonnier ............... | 604/189 |
| 2004/0024368 A1 * | 2/2004 | Broselow ............... | 604/207 |
| 2004/0059299 A1 | 3/2004 | Moller | |
| 2004/0199125 A1 * | 10/2004 | Miller et al. ............ | 604/232 |
| 2004/0210199 A1 | 10/2004 | Atterbury et al. | |
| 2004/0267207 A1 | 12/2004 | Veasey et al. | |
| 2005/0101905 A1 | 5/2005 | Merry | |
| 2005/0113765 A1 | 5/2005 | Veasey et al. | |
| 2005/0119622 A1 | 6/2005 | Temple | |
| 2006/0153693 A1 | 7/2006 | Fiechter et al. | |
| 2007/0197978 A1 | 8/2007 | Wortham | |
| 2007/0215149 A1 | 9/2007 | King et al. | |
| 2009/0230015 A1 * | 9/2009 | Harrison ............... | 206/571 |
| 2009/0275916 A1 | 11/2009 | Harms et al. | |
| 2010/0038273 A1 * | 2/2010 | Johnson ............... | B65D 25/34 206/459.5 |

FOREIGN PATENT DOCUMENTS

| | | | | |
|---|---|---|---|---|
| EP | WO9947062 | * | 9/1999 | ............ A61B 19/00 |
| EP | 1923083 | | 5/2008 | |
| WO | 99/38554 | | 8/1999 | |
| WO | 99/47062 | | 9/1999 | |
| WO | 01/10484 | | 2/2001 | |
| WO | 03/086511 | | 10/2003 | |
| WO | 2009/107224 | | 9/2009 | |
| WO | 2010/006870 | | 1/2010 | |

OTHER PUBLICATIONS

International Search Report and Written Opinion for Int. App. No. PCT/EP2011/054876, completed Jul. 7, 2011.

* cited by examiner

SET OF MEMBERS FOR A DRUG DELIVERY DEVICE, DRUG DELIVERY DEVICE AND SET OF DRUG DELIVERY DEVICES

CROSS REFERENCE TO RELATED APPLICATIONS

The present application is a U.S. National Phase Application pursuant to 35 U.S.C. § 371 of International Application No. PCT/EP2011/054876 filed Mar. 30, 2011, which claims priority to European Patent Application No. 10158674.1 filed on Mar. 31, 2010. The entire disclosure contents of these applications are herewith incorporated by reference into the present application.

FIELD OF INVENTION

This disclosure relates to a set of members for a drug delivery device, a drug delivery device and a set of drug delivery devices.

BACKGROUND

Drug delivery devices of similar appearance may be provided for delivering different types of drugs. In particular, a single user may use devices comprising a similar exterior shape for dispensing different drugs. It is desirable that mixing-up different devices and, hence, different drugs is prevented.

A drug delivery device is described in document EP 1 923 083 A1, for example.

Cartridges are generally marked with details of the medicament that they contain, and may be differentiated with a specific color for that medicament. Although the cartridge itself is marked with details of the medicament that it contains, this marking may be difficult to see after the cartridge is loaded into the device, so the user may select the wrong device, and dispense the wrong medicament. It would therefore be advantageous for a reusable drug delivery device to be marked with a medicament differentiation. However, with a differentiated reusable device there is a risk that the user might load a cartridge in the wrong device, and then rely on the differentiation on the device rather than reading the cartridge label, and so dispense the wrong medicament. Alternatively, all detachable parts of the reusable device might be dedicated (or mechanically coded) to each other, but without any differentiation. For example, the cartridge might be coded to the cartridge holder, the cartridge holder to the dose setting mechanism, and the cap to the dose setting mechanism. The risk of a fully dedicated device is that it might be difficult to understand, so the user might apply excessive force to assemble the device, and damage the coding so that a cartridge fits into an incorrect device.

SUMMARY

It is an object of the present disclosure to facilitate provision of novel, preferably improved, drug delivery devices, for example devices providing high safety for a user.

This object may be achieved by the subject matter of the independent claims. Further features and advantageous embodiments are the subject matter of the dependent claims.

According to one aspect, a set of members for a drug delivery device is provided. The set may comprise at least two components for the device. Both components may be provided with a marking. The markings are expediently substantially equivalent or identical.

By means of the markings provided on the components of the device, information, in particular information about the device, may be provided to the user. The respective marking may identify a particular drug held in the device. In this way, the user may verify whether he uses the right device and, in particular, whether the device holds the right drug. The respective marking may be adapted and arranged to be viewed and/or contacted by the user any time during operation of the device. In particular, one of the markings may be arranged to be contacted or viewed by the user when setting the dose. The other one of the markings may be arranged to be contacted or viewed by the user when delivering the set dose. In this way, during operation of the device, the user may always contact or view at least one marking.

According to an embodiment, the markings each comprise at least one tactile marking.

Tactile markings may be especially suited for users with impaired vision, e.g. users suffering from diabetes. Tactile markings may be recognized by the user even if he is no longer able to confirm visually that he is using the right device. The respective tactile marking may be adapted and arranged to be viewed and/or contacted by the user any time during operation of the device. In particular, one of the tactile markings may be arranged to be contacted or viewed by the user when setting the dose. The other one of the tactile markings may be arranged to be contacted or viewed by the user when delivering the set dose. In this way, during operation of the device, the user may always contact or view one marking The respective tactile marking may comprise one or more structural elements which may be grouped to form the tactile marking Preferably, said structural elements comprise a structural depth great enough to generate a tactile feedback when a user contacts the respective tactile marking.

According to an embodiment, the markings each comprise at least one colour marking.

Additionally or alternatively to the tactile marking, the markings may comprise a colour. By means of a colour marking the user may realize easily to which type of drug the respective marking relates. Colours may be recognized even by users with seriously impaired eyesight. While preparing the device for operation and also during operation of the device the respective colour marking may be viewed by the user.

According to an embodiment, the markings each comprise at least one text marking.

According to an embodiment, the at least one text marking comprises a name of a drug for the device, in particular a drug held in a cartridge of the device.

Thus, additionally or alternatively to the tactile marking and/or colour marking, the respective marking may comprise a text or text-like marking, e.g. a marking comprising a text, a number and/or a character. The respective text or text-like marking may comprise the name of the drug that is used in the drug delivery device.

According to an embodiment, the markings each comprise at least one symbol.

Additionally or alternatively to the tactile marking, the colour marking and/or the text marking, the respective marking may comprise a symbol which may be specifically associated with the particular drug used in the drug delivery device. The symbol may be a logo associated with the drug, for example.

According to an embodiment, the at least two components comprise a main housing for the drug delivery device and/or one, two, three or more of the following additional components: A dose button for the drug delivery device. A cap for the drug delivery device. A cartridge for the drug delivery device. A cartridge holder for the drug delivery device. The respective additional component may be connectable, preferably releasably connectable, to the main housing. Two, three, four or more of the at least two components are provided with substantially equivalent or identical markings In the following text one of the markings, in particular the marking provided on the main housing of the device, is referred to as "device marking". The at least other one of the markings, preferably the two, three, four or more markings, provided on the additional components of the device, is referred to as "component marking", respectively. Preferably, the device marking is arranged to be contacted and/or viewed by the user when setting a dose of the drug which is to be delivered by the device. Preferably, the component marking is arranged to be contacted and/or viewed by the user when preparing the device for setting and/or when delivering the set dose.

The substantially equivalent or identical device marking and component marking may identify one particular type of drug held in the cartridge of the device. This may increase the user's confidence that he is administering the correct drug. Any time during operation of the device, e.g. during setting and delivery of the dose and/or while preparing the device for operation, the user may contact or at least view one of the device marking and the component markings.

The device marking may comprise a marking having a different outer appearance compared to the component marking For example, the device marking may comprise a tactile marking. The component marking may comprise a colour, a symbol and/or a text marking, for example, or vice versa. Though the outer appearance of the markings may be different, the respective marking may be adapted and arranged to provide the same information to the user, e.g. information, about the device and, in particular, the drug held in the cartridge of the device.

However, it is preferred that every type of device marking, e.g. tactile, colour, text or symbol, has a corresponding component marking of the same type.

In case the device marking and the component marking each comprise a tactile marking, the substantially equivalent or identical tactile markings may comprise an identical number and/or an identical shape of one or more or all structural elements which are grouped to form the tactile device marking and component marking Substantially equivalent or identical tactile markings may comprise a different size and/or a different material of the structural elements. However, as described above, the substantially equivalent or identical tactile markings expediently provide the same information, in particular recognizably equivalent tactile feedbacks, to the user.

In case the device marking and the component marking each comprise a colour marking, the substantially equivalent or identical colour markings may comprise the same colours or at least similar colours, in particular colour ranges which are neighbouring in the electromagnetic spectrum. The substantially equivalent or identical colour markings provide the same information, in particular information about the drug, to the user.

In case the device marking and the component marking each comprise a text marking, the substantially equivalent or identical text markings may comprise the same text or different texts containing the same information like an expression and an abbreviation of this expression. However, the component text marking and the device text marking may comprise a different size and/or shape, for example.

According to an embodiment, the main housing comprises a housing body. The main housing may comprise a housing insert. The housing insert may be releasably connected to the housing body. A marking of the main housing, in particular the device marking, may be provided on the housing insert.

The housing insert and the marking may be formed unitarily. The housing insert may be an exchangeable component of the device. Accordingly, the housing insert comprising the marking may be replaceable by a replacement housing insert. The replacement housing insert may be provided with a different marking, e.g. a marking identifying a different drug. This may be especially applicable for a re-usable drug delivery device and, in particular, for a drug delivery device adapted to dispense different drugs.

According to a further embodiment, the marking is provided on the housing body. Accordingly, at least one marking may be provided on a part of the device, which is not exchangeable. In this case, the housing insert may be redundant. This may be especially applicable for a disposable drug delivery device and/or a drug delivery device adapted to hold only one particular drug. In this case, the housing body may form the main housing.

According to a further aspect a drug delivery device is provided. The drug delivery device may comprise a main housing. The drug delivery device may comprise one, two, three or more of the following additional components of the previously described set of members: A dose button for the drug delivery device. A cap for the drug delivery device. A cartridge for the drug delivery device. A cartridge holder for the drug delivery device. The respective additional component of the set of members may be connected, preferably releasably connected, to the main housing at least in a storage mode of the device, e.g. a mode when the device stored, in particular between subsequent operation modes of the device or when a different drug contained in a different device is dispensed. One of the markings of the components of the set of members, e.g. the device marking, may be provided on the main housing. An other one of the markings, e.g. the component marking, may be provided on at least one, preferably on two ore more, of the additional components.

The main housing which is provided with the marking, may be configured to be contacted or viewed by the user when setting a dose of a drug. At least one of the dose button, the cartridge, the cartridge holder and the cap, in particular the additional components which are provided with the component marking, may be configured to be contacted or viewed by the user when preparing the device for operation and/or when delivering the set dose. The substantially equivalent or identical markings, in particular the component marking and the device marking, may identify the drug delivery device and, in particular, one particular drug held in the device.

According to a further aspect a set of drug delivery devices is provided. The set may comprise two, three, or more drug delivery devices. These devices may comprise a similar exterior shape and/or colour. The respective device may comprise a corresponding set of members as described above. Components of sets of members of different devices are expediently provided with different markings Differently marked components may be part of devices holding different drugs. Differently marked drug delivery devices always hold different drugs.

In an embodiment of the set of drug delivery devices the components of sets of members of different devices may be provided with same (identical) markings, and same marked components may be part of devices holding same drugs.

In a further embodiment of the set of drug delivery devices at least one respective device is disposable and another respective device is reusable.

In a further embodiment of the set of drug delivery devices the sets of members have mechanical couplings coded such that only members with the same markings can be connected together.

In a further embodiment of the set of drug delivery devices a drug specific cartridge holder is provided with coupling features corresponding to a specific cartridge, such that only the specific cartridge can be inserted into the drug specific cartridge The components of the previously described set of members, in particular, components comprising substantially equivalent or identical markings, may be assembled to form one single drug delivery device. In particular, components of one particular device may comprise substantially equivalent or identical markings. One component marking may be provided on the dose button, for example. An additional component marking may be provided on the cap. The device marking may be provided on the housing insert, for example.

The different drug delivery devices may be customized to the drug to be delivered by providing differently marked components. In particular, the different markings and the differently marked additional components may be adapted to identify the drug held in the respective device.

The user may choose a first device and, thus, a first drug he wants to use by viewing and/or contacting the markings provided on the components of this device. The user may contact and/or move one component of said first device with respect to the housing, hence preparing the first device for operation. Thereby, the user contacts and/or views at least one of the markings, e.g. the device marking which may be provided on the housing insert, for example. Afterwards, the user may put the first device aside, e.g. for preparing a second device comprising differently marked additional components which identify a second drug held in the second device, for operation. Later on, when the user wants to dispense the first drug, the user grabs one of the devices previously prepared for operation. By means of the markings, in particular the device marking and the component markings, provided on the components of said device, the user can verify at once, whether he has grabbed the right device, i.e. the first device holding the first drug. Hence, provision of a device providing high safety for the user is facilitated.

Preferably, all components of the respective device being provided with a marking, are releasably connected to the housing body of the respective device. The housing body may be free of a marking. Accordingly, the differently marked drug delivery devices may comprise equally formed housing bodies, e.g. a housing body comprising the same exterior shape, colour and/or size. This may help to reduce manufacturing cost for the set of drug delivery devices as a single type of housing body may be used for different drug delivery devices. Furthermore, the basic shape and/or colour of the additional components except for the markings may be the same for all devices. The different additional components may comprise a different tactile, colour, symbol and/or text marking for identifying a different drug held in the second device.

Together with the set of different drug delivery devices a table may be provided to the user to link the respective marking of the components of the respective device to the drug held in said device.

In the following, features described in connection with the drug delivery device, with the set of components for the drug delivery device and with the set of drug delivery devices may be combined with each other and with features described below. For example, features, which are relevant for the drug delivery device, may be relevant for the set of components and for set of devices, as well.

According to an embodiment, the main housing comprises a window section. The housing insert may comprise the window section. The device marking may be arranged offset, preferably distally offset, from the window section.

The window section may be adapted and arranged to allow a user to view through the housing insert and, preferably, from the outside of the main housing to the inside of the main housing. Thus, the user may gather information which is displayed through the window section, e.g. information about the size of the set dose.

According to an embodiment, the device comprises a label. The label may be releasably or permanently attached to the main housing, in particular to the housing insert, for example. Alternatively, the label may be arranged on any other part of the device, e.g. on the cartridge holder. One of the markings may be provided on the label.

The label may be easily removable from the device and, thus, may be replaceable by an other label comprising a different marking, for example a component marking, e.g. indicating a different drug.

According to an embodiment, the additional component comprises a cartridge holder. The cartridge holder may be connected, preferably releasably connected, to the housing body. The component marking or an additional component marking may be provided on the cartridge holder.

The cartridge holder may be an exchangeable component of the device. Accordingly, the cartridge holder may be removable from the device and, thus, may be replaceable by an other cartridge holder, e.g. a cartridge holder comprising a different component marking for example for indicating a different drug. This may be especially applicable for a re-usable drug delivery device.

According to an embodiment, the additional component comprises a dose button. The dose button may be adapted and arranged to be contacted by the user for delivering the set dose. The component marking or an additional component marking may be provided on an actuation surface of the dose button, e.g. a surface of the dose button adapted to be contacted for delivering the dose.

By viewing and/or contacting the component marking provided on the dose button, the user may be able to identify the drug held in the device. The actuation surface comprising the component marking or an additional component marking may be contacted, preferably pressed, by the user for starting the drug delivery action.

According to an embodiment, the additional component comprises a cap. The cap may be releasably connectable to the main housing. The cap may be adapted and arranged to cover a dispensing end of the drug delivery device, in particular in a storage mode of the device. For operation, the dispensing end is expediently uncovered. The cap may be adapted to cover the cartridge holder. The component marking or an additional component marking may be provided on an outer surface of the cap.

By viewing and/or contacting the component marking provided on the cap, the user may identify at once the drug held in the device and hence, if he uses the right device. For making the device ready for operation, the cap may be detached from the device. For this purpose, the user contacts the outer surface of the cap, thereby he contacts or views the component marking provided on the outer surface of the cap. The user may compare the component marking or the feedback said marking generates with the device marking or the feedback thereof he contacts or views later on when setting the dose. Furthermore, if applicable, the user may compare said component marking with the component marking arranged on the actuation surface of the dose button, which the user contacts after setting and, in particular, for delivering the set dose. The said markings, e.g. the component marking, the additional component marking and the device marking, are expediently substantially equivalent or identical. Accordingly, any time the user contacts or at least views the device, e.g. during preparation of the device for operation, during setting of the dose and during delivery of the set dose, the user can control that he uses the correct device.

According to an embodiment, one, more or all of the additional components of the drug delivery device which comprise a marking are exchangeable.

In this way, the markings may be replaceable by a different marking for identifying different drugs held in the device. This is especially applicable for re-usable drug delivery devices.

According to an embodiment, the drug delivery device is a pen-type device, in particular a pen-type injector.

Alternatively, the drug delivery device may be an electromechanical device. The drug delivery device may also have a different form or geometry, either for use as a hand held device or as a body worn device, such as an infusion pump. A hand held drug delivery device is shown for example in patent application WO03051428 which is incorporated herein by reference.

According to an embodiment, the respective device is disposable.

According to an embodiment, the respective device is re-usable.

The insert components of the device comprising the respective marking may be releasably connected to the housing body of the device. Accordingly, the device may be adapted to hold a plurality of different drugs. The respective drug may be, preferably unambiguously, identified by the marking provided on the components of the device.

According to an embodiment, a storage unit, preferably a storage unit for a drug delivery device such as for the previously described drug delivery device, is provided. The storage unit may comprise a case, e.g. a carry case, for the device. The case is adapted to receive and retain the device, in particular to secure the device within the case. The case is expediently adapted to provide storage and protection to the device, in particular from environmental influences when the device is retained in the case. Additionally or alternatively, the storage unit may comprise a drug packaging for a drug, preferably for a cartridge containing the drug, for the device. The case and/or the drug packaging may be provided with at least one storage marking. The storage marking may be a tactile marking. Additionally or alternatively, the storage marking may be a colour, a text and/or a symbol marking The storage marking may be substantially equivalent or identical to at least one of the markings, e.g. the device marking and/or the component marking, provided on the device or the cartridge of the device.

The case may be adapted and arranged to receive the device in an interior of the case. The storage marking may provide the same information to the user, in particular information about the drug held in the device, as the markings, in particular the device marking an the component marking, on the device.

A storage marking, if applicable an additional storage marking, may be provided on an outer surface of the drug packaging. The drug packaging may be retained and/or secured together with the device in the case for the drug delivery device. Accordingly, additional drug may be supplied in the case in addition to drug contained in the device, e.g. by means of a replacement cartridge containing the drug. The storage marking may provide the same information to the user, in particular information about the drug held in the drug packaging, as the device and the component marking of the device, for example on the cartridge of device.

According to a preferred embodiment, a set of members for a drug delivery device is provided comprising at least two components for the device, wherein both components are provided with a marking, the markings being substantially equivalent or identical.

The, in particular substantially equivalent or identical, markings allow the user to gather information about the device and, in particular, about the drug held in the device. For identifying a second drug delivery device holding a second particular drug, a second set of members having a different marking may be provided.

In an example embodiment, a differentiated and dedicated drug delivery device is described, where at least some parts of the device are differentiated for the medicament, and dedicated to each other, for example by mechanical coding.

Of course, features described above in connection with different aspects and embodiments may be combined with each other and with features described below.

Further features, advantages and refinements become apparent from the following description of the exemplary embodiments in connection with the accompanying figures.

BRIEF DESCRIPTION OF THE FIGURES

Like elements, elements of the same kind and substantially equivalent or identically acting elements may be provided with the same reference numerals in the figures.

DETAILED DESCRIPTION

Figure 1:
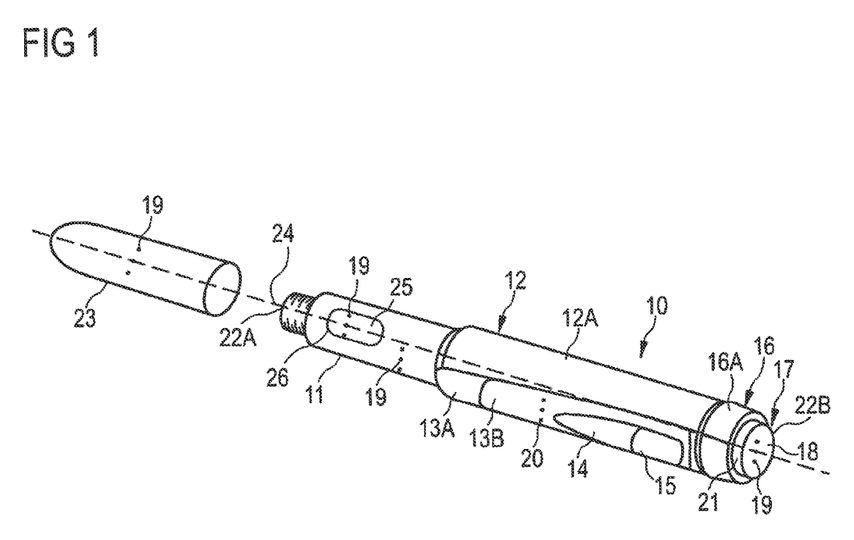
FIG. 1 schematically shows a perspective side view of an exemplary embodiment of a drug delivery device, FIGS. 2A through 2C schematically show a set of three differently marked drug delivery devices, FIGS. 3A through 3F schematically show parts of the drug delivery device of FIG. 1.

In FIG. 1 an exemplary embodiment of a drug delivery device 10 is shown. The drug delivery device 10 may be an injection device. The drug delivery device 10 may be a pen-type device, in particular a pen-type injector. The device 10 may be a disposable or a re-usable device. Preferably, the device 10 is re-usable. The device 10 may be configured to dispense fixed doses of a drug, in particular doses which may not be varied by the user, or variable, preferably user-settable, doses of the drug. The drug delivery device 10 may be a manually driven device. Alternatively, the drug delivery device 10 may be an electrically driven device.

The drug delivery device comprises a main housing 12. The main housing 12 comprises a tubular shape. The main housing 12 is configured to house members of a drive mechanism of the drug delivery device 10. The drive mechanism is adapted to drive members, e.g. a piston rod (not explicitly shown) arranged within the main housing 12 for dispensing the set dose.

The drug delivery device 10 and the main housing 12 have a distal end and a proximal end. The term "distal end" designates that end of the drug delivery device 10 or a component thereof which is or is to be arranged closest to a dispensing end of the drug delivery device 10. The term "proximal end" designates that end of the device 10 or a component thereof which is or is to be arranged furthest away from the dispensing end of the device 10. The distal end and the proximal end are spaced apart from one another in the direction of an axis 24. The axis 24 may be the main longitudinal axis of the device 10.

The drug delivery device 10 comprises a housing body 13A. The housing body 13A is part of the main housing 12 of the device 10. The drug delivery device 10 comprises a cartridge holder 11. The cartridge holder 11 is connectable, preferably releasably connectable, to the housing body 13A. Preferably, the cartridge holder 11 is releasably connected, for example screwed, to the housing body 13A to allow introduction of a replacement cartridge holder 11 into the device 10. In particular, the cartridge holder 11 is exchangeable.

Each of the parts of the pen system that are intended to be separated and reconnected by users may each be provided with substantially equivalent or identical markings and tactile features. Furthermore, each of the pen system parts that are intended to be separated and reconnected by users may be provided with unique mechanical coupling features, such that only the correctly matching substantially equivalent or identical marked pen system parts can be fitted together. Typically, the parts of a pen system that are separable and reconnectable by users are the cap from the drug delivery housing and in the case of a reusable drug delivery device, also the cartridge holder from the drug delivery housing. To further increase safety for the user, a drug specific cartridge holder may be provided with unique mechanical coupling features for a corresponding specific drug cartridge, such that only the correct drug cartridge can be inserted.

The drug delivery device 10 comprises a housing insert 13B. The housing insert 13B is part of the main housing 12 of the device 10. The housing insert 13B is inserted into and, permanently or releasably, connected to the housing body 13A of the main housing 12. Preferably, the housing insert 13B is releasably connected, for example snap-fitted, to the housing body 13A to allow insertion of a replacement housing insert 13B into the housing body 13A. In particular, the housing insert 13B is exchangeable. The housing insert 13B is preferably arranged in a recessed section of the housing body 13A (not explicitly shown). Thus, the housing insert 13B does not increase the radial extension of the device 10. Preferably, the housing insert 13B ends flush with the housing body 13A on an outer surface of the main housing 12.

The housing insert 13B comprises a window section 15. The window section 15 is preferably arranged in the proximal end section of the housing insert 13B. The window section 15 comprises a transparent or translucent window. The window may enable the user to view through the housing insert 13B. Preferably, the housing body 13A comprises an aperture with which the window section 15 overlaps. Thus, the user may view in the window section 15 through the wall of the main housing 12 to a component housed therein, e.g. to a dose dial member 16 (which is described later on) comprising, for example, symbols for providing dosage information.

The housing insert 13B comprises a label section. The label section is arranged offset, preferably distally offset, from the window section 15. The label section is configured for holding a label 14. The label 14 may be releasably or permanently attached to the label section. Preferably, the label 14 is releasably attached to the label section. Accordingly, the label 14 is exchangeable.

The main housing 12 comprises an outer lateral surface 12A. The outer lateral surface 12A connects a distal end-face 22A of the drug delivery device 10, e.g. a distal end of the cartridge holder 11, and a proximal end-face 22B of the drug delivery device 10, e.g. a surface formed by a part of a drive mechanism of the device 10 which is explained later on in more detail, with one another.

The device 10 comprises a cartridge 25. The cartridge 25 is retained in the cartridge holder 11. Alternatively, the cartridge holder 11 can be dispensed with and the cartridge 25 can be directly connected to the housing body 12. The cartridge holder 11 comprises a window 26. A part of the cartridge 25 is visible through the window 26. The cartridge holder 11 stabilizes the cartridge 25 mechanically. The cartridge 25 may hold one or a plurality of doses of a drug. The term "drug" as used herein preferably means a pharmaceutical formulation containing at least one pharmaceutically active compound having a molecular weight up to 1500 Da, or a pharmaceutically active peptide, protein, DNA, RNA, antibody, enzyme, hormone or oligonucleotide, or a mixture thereof, preferably comprising at least one peptide, further preferred a peptide for the treatment of diabetes mellitus or complications associated with diabetes mellitus such as diabetic retinopathy, especially preferred human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin, Lys(B3), Glu(B29) human insulin, Lys(B28), Pro(B29) human insulin, Asp(B28) human insulin, human insulin, wherein proline in position B28 is replaced by Asp, Lys, Leu, Val or Ala and wherein in position B29 Lys may be replaced by Pro, Ala(B26) human insulin, Des(B28-B30) human insulin, Des(B27) human insulin and Des(B30) human insulin.

Insulin derivates are for example B29-N-myristoyl-des (B30) human insulin, B29-N-palmitoyl-des(B30) human insulin, B29-N-myristoyl human insulin, B29-N-palmitoyl human insulin, B28-N-myristoyl LysB28ProB29 human insulin, B28-N-palmitoyl-LysB28ProB29 human insulin, B30-N-myristoyl-ThrB29LysB30 human insulin, B30-N-palmitoyl-ThrB29LysB30 human insulin, B29-N-(N-palmitoyl-Y-glutamyl)-des(B30) human insulin, B29-N-(N-lithocholyl-Y-glutamyl)-des(B30) human insulin, B29-N-(ω-carboxyheptadecanoyl)-des(B30) human insulin and B29-N-(ω-carboxyheptadecanoyl) human insulin.

Exendin-4 preferably means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39), des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative, or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2,
or a pharmaceutically acceptable salt or solvate of any one of the afore-mentioned Exedin-4 derivative.

Hormones are preferably hypophysis hormones or hypothalamus hormones or regulatory active peptides and their antagonists as listed in Rote Liste, ed. 2008, Chapter 50. Examples of hormones are Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. Ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The drug delivery device 10 may comprise a needle assembly (not explicitly shown), comprising a needle. The needle assembly may be releasably attached to the cartridge holder 11, for example by means of a thread. The needle, when attached, may be in fluid communication with the interior of the cartridge 25.

A bung (not explicitly shown) is moveably retained in the cartridge 25. The bung seals the cartridge 25 proximally. Movement of the bung in the distal direction with respect to the cartridge 25 causes a dose of the drug to be dispensed from the cartridge 25, provided that fluid communication was established between the interior and the exterior of the cartridge 25.

The device 10 comprises the previously mentioned drive mechanism. The drive mechanism is arranged and retained at least partly within the main housing 12 of the drug delivery device 10. The drive mechanism comprises the previously mentioned dose dial member 16. The dose dial member 16 is releasably or permanently connected to the main housing 12. The dose dial member 16 may be threadedly engaged with the housing body 13A. The dose dial member 16 may be provided with dose numbers on an outer surface thereof. The dose dial member 16, in particular its outer surface, may be viewed through the window aperture of the housing insert 13B. The dose number currently displayed in the window aperture indicates the size of the currently set dose. This size may be varied by moving the dose dial member 16 with respect to the main housing 12. Thereby, the displayed number will change.

The drive mechanism comprises a dose button 17. The dose button 17 is, permanently or releasably, connected to the dose dial member 16. Preferably, the dose button 17 is releasably secured, for example snap-fitted, to the dose dial member 16 to allow a replacement dose button 17 to be used in the device 10. Thus, the dose button 17 is expediently exchangeable. The dose dial member 16 may be rotatable with respect to the dose button 17, e.g. for dispensing the set dose, due to mechanical cooperation of the dose button 17 and the dose dial member 16. The dose button 17 is secured against axial movement with respect to the dose dial member 16. A clutch 30 may be provided between the dose button 17 and the dose dial element 16. If the clutch is engaged, the dose dial element 16 and the dose button 17 are rotationally locked to each other. The clutch is preferably engaged when setting the dose. If the clutch is disengaged, relative rotation between dose button 17 and dose dial element 16 is permitted. The clutch is preferably disengaged when delivering the dose, e.g. by a movement of the dose button 17 with respect to the dose dial element 16 which is triggered by the user pressing on the dose button 17.

The dose dial member 16 is actuatable for setting a dose of the drug. In particular, the dose dial member 16 is rotatable and/or displaceable in the proximal direction with respect to the main housing 12 for setting the dose. The dose dial member 16 comprises a setting surface 16A. The setting surface 16A comprises the outer lateral surface of the dose dial member 16. The setting surface 16A is gripped by the user for moving the dose dial member 16 with respect to the main housing 12 for setting the dose.

The dose dial member 16 may be rotatable with respect to the main housing 12 for setting the dose. In particular, the dose button 17 may follow rotation of the dose dial member 16 for setting the dose due to mechanical cooperation of the dose dial member 16 and the dose button 17, e.g. due to the clutch 30 between these two elements which is engaged when the dose is set, for example two sets of mutually engaging dog teeth. During rotation of the dose dial member 16 for setting the dose, the dose dial member 16 and, hence, the dose button 17, are moved in the proximal direction with respect to the main housing 12 due to mechanical cooperation, in particular threaded engagement, of the dose dial member 17 and the main housing 12, preferably an inner surface thereof.

The dose button 17 is actuatable for dispensing the set dose. In particular, the dose button 17 is axially displaceable in the distal direction with respect to the main housing 12 for dispensing the dose. Alternatively, in case of an electrically driven device, the dose button 17 is contactable for dispensing the dose.

The dose button 17 comprises an actuation surface 18. The actuation surface 18 forms the proximal end-face 22B of the device 10. The user contacts the actuation surface for dispensing the set dose. For example, the user pushes onto the actuation surface for displacing the dose button 17 and, hence, the dose dial member, distally. Distal displacement of the dose dial member 16 is converted into rotational movement of the dose dial member 16 with respect to the main housing 12 due to mechanical cooperation of the dose dial member 16 and the main housing 12. When the dose is dispensed, the dose dial member 16 may rotate with respect to the dose button 17. For this purpose, the previously mentioned clutch is expediently disengaged, for example by an axial disengagement movement of the dose button 17 with respect to the dose dial member 16, thereby disengaging the clutch.

The drug delivery device 10 comprises a cap 23. The cap 23 is connectable to the main housing 12. In particular, the cap 23 is securable to the distal end of the housing body 13A. In a storage mode of the device 10, the cap 23 is adapted and arranged to cover the dispensing end of the drug delivery device 10 including, if applicable, the previously mentioned needle assembly. The cap 23 is configured to cover the cartridge holder 11. For preparing the device 10 for operation and, in particular, for bringing the device into an operational mode, e.g. a mode which allows for setting and delivering drug, the cap 23 is unsecured from the housing body 13A to uncover the cartridge holder 11 and, if applicable, the needle assembly.

The drug delivery device 10 comprises at least two markings 19, 20. The drug delivery device 10 may comprise at least one marking provided on the main housing 12 or an element of the main housing 12. Said marking is in the following referred to as "device marking" 20. The drug delivery device 10 may comprise at least one marking provided on at least one, preferably two or more, additional components of the device 10, e.g. the dose button 17, the cartridge 25, the cartridge holder 11 and/or the cap 23. The respective marking is in the following referred also to as "component marking" 19. Furthermore, a marking, for example a component marking 19, may be provided on the label 14. The device marking 20 and the component marking 19 are provided on an outer surface of the device 10, respectively.

The respective marking 19, 20 may comprise a tactile marking. Tactile markings may be especially suited for users with impaired vision, e.g. users suffering from diabetes. For blind users, the tactile markings may provide letters or words in Braille. Alternatively, the tactile markings may be different from letters or words in Braille.

The tactile marking may comprise one or a plurality of structural elements, e.g. elevations. Preferably, said structural elements comprise a structural depth great enough to generate a tactile feedback when a user contacts the respective tactile marking The structural elements may be grouped to form a certain structure of the tactile marking which is described later on in more detail. Additionally or alternatively to the tactile marking, the respective marking 19, 20 may comprise a colour marking, e.g. a colour dot or a coloured elevation. Additionally or alternatively, the respective marking 19, 20 may comprise a text marking, e.g. a trade name or the name of an active compound of the drug. The device marking 20 may comprise the name of the drug held in the cartridge 25 of the drug delivery device 10. Additionally or alternatively the respective marking 19, 20 may be a symbol or character that is specifically associated with the particular drug used in the drug delivery device 10, e.g. a drug logo. The respective marking 19, 20 is configured to be viewed and/or contacted by the user.

The tactile marking 19, 20 may comprise a structure. For example, both the device marking 20 and the component marking 19 may comprise at least one insular bump (see FIGS. 3A and 3B). Alternatively, each of the device marking 20 and the component marking 19 may comprise a plurality of bumps arranged in a respective group to form a structure for the respective marking 19, 20 (see FIGS. 3E and 3F).

The component marking 19 and the device marking 20 comprise substantially equivalent or identical markings, e.g. substantially equivalent or identical tactile, colour, text, symbol and/or character markings In particular, the tactile device marking 20 and the component marking 19 may comprise the same shape and/or relative arrangement of the structural elements of the respective marking 19, 20 with respect to each other. However, tactile markings 19, 20 may comprise a different size and/or material. Substantially equivalent or identical colour markings 19, 20 may comprise similar colours, in particular colour ranges which are neighbouring in the electromagnetic spectrum, for example.

The markings 19, 20 are adapted to generate a similar, preferably the same, tactile and/or visual feedback within the user. In particular, the device marking 20 and the component marking 19 provide the same information to the user. The device marking 20 and the component marking 19 are preferably adapted and arranged to signal to the user which drug is contained in the device 10 comprising the markings 19, 20. One set of substantially equivalent or identical component and device markings 19, 20 preferably identifies one particular device 10 and, hence, one particular drug held in the cartridge 25 of said device 10.

The device marking 20 is provided on components of the device 10 which are arranged to be contacted by the user when setting a dose of the drug, e.g. in a dose setting section of the device 10. In particular, the device marking 20 is provided on at least one part of the main housing 12 as describe above. The device marking 20 is provided on the outer lateral surface 12A of the main housing 12. The device marking 20 may be milled, lathed or moulded into the outer lateral surface of the main housing 12 for this purpose.

The device marking 20 is provided on an exchangeable part of the main housing 12. According to the embodiment shown in FIG. 1, the device marking 20 is provided on the housing insert 13B, in particular on the outer surface of the housing insert 13B. The device marking 20 is provided in a distal end section of the housing insert 13B such that the user can easily contact the device marking 20 when he holds the device 10 when setting a dose of the drug, e.g. between thumb and index finger of the left hand.

The component marking 19 is provided on an exchangeable component of the device 10. The component marking 19 is preferably formed unitarily with the exchangeable components of the device 10. The component marking 19 may be milled, lathed or moulded into an outer surface of said components. For one device marking 20 preferably at least one corresponding, in particular substantially equivalent or identical, component marking 19 is provided. It is preferred that the device 10 comprises two component markings 19, as shown in FIG. 1.

At least one component marking 19 is provided on a part of the device 10 which is contacted by the user when delivering the set dose of the drug, e.g. in a dose delivery section of the device 10. According to the embodiment shown in FIG. 1, said component marking 19 is provided on the dose button 17. The component marking 19 is provided on the actuation surface 18, e.g. the proximal end-face, of the dose button 17. For delivering the set dose, the user contacts the actuation surface 18. The user may push onto the actuation surface 18 for displacing the dose button 17 with respect to the main housing 12, thereby contacting the component marking 19 arranged thereon.

An additional component marking 19, e.g. tactile, colour and/or text marking, may be provided on at least one component of the device 10 which is moveable with respect to the main housing 12 for preparing the device 10 for setting and, in particular, for delivering a dose of a drug. As shown in FIG. 1, said component marking 19 is provided on the cap 23, in particular on an outer surface of the cap 23. For making the device 10 ready for operation, the user unsecures the cap 23 from the main housing 12, thereby contacting the component marking 19.

As shown in FIG. 1, an additional component marking 19 is provided on the cartridge holder 11, in particular on the outer lateral surface of the cartridge holder 11. This additional marking 19 is provided in the proximal end section of the cartridge holder 11. Additionally or alternatively, the component marking 19 may be provided on the cartridge 25. The component marking 19 of the cartridge 25 may be visible through the window 26 of the cartridge holder 11.

Furthermore, an additional component marking 19 may be provided on the previously mentioned label 14 which is, for example, releasably attached to the outer surface of the housing insert 13B, in particular in the label section. The label 14 may be arranged distally offset from the window section 15. Alternatively, the label 14 carrying the component marking 19 may be releasably attached to any part of the device 10 which can, for example, be viewed and/or contacted by the user when preparing the device 10 for operation and/or when delivering the dose.

During operation of the device 10, the user can verify by means of the markings 19, 20, whether he uses the right device 10.

The device marking 20 and the component marking 19 are preferably each provided on components of the device 10 which are exchangeable, e.g. on the housing insert 13B, on the label 14, on the cartridge holder 11, on the cartridge 25, on the cap 23 and/or on the dose button 17. This may be especially suitable for a re-usable drug delivery device 10. If a replacement cartridge holding a different drug should be applied in the device 10, the components of the device 10 provided with the device marking 20, e.g. the housing insert 13B and/or the cartridge holder 11, and with the component marking 19, e.g. the dose button 17 and/or the cap 23, may be exchanged. In particular, the housing insert 13B may be replaced with a replacement housing insert which is provided with a marking 19, 20 for identifying the different drug held in the replacement cartridge. Furthermore, the cartridge holder 11 may be replaced with a replacement cartridge holder. The dose button 17 may be replaced with a replacement dose button. The cap 23 may be replaced with a replacement cap. Said replacement components each comprise a different marking 19, 20 for identifying the different drug held in the replacement cartridge.

The device marking 20 may be provided permanently on the housing body 13B. Accordingly, the device marking 20 may be provided on a non-exchangeable part of the device 10. This embodiment may be especially suitable for a disposable drug delivery device 10 or a device 10 adapted to hold and dispense only one particular drug.

Figure 2A:
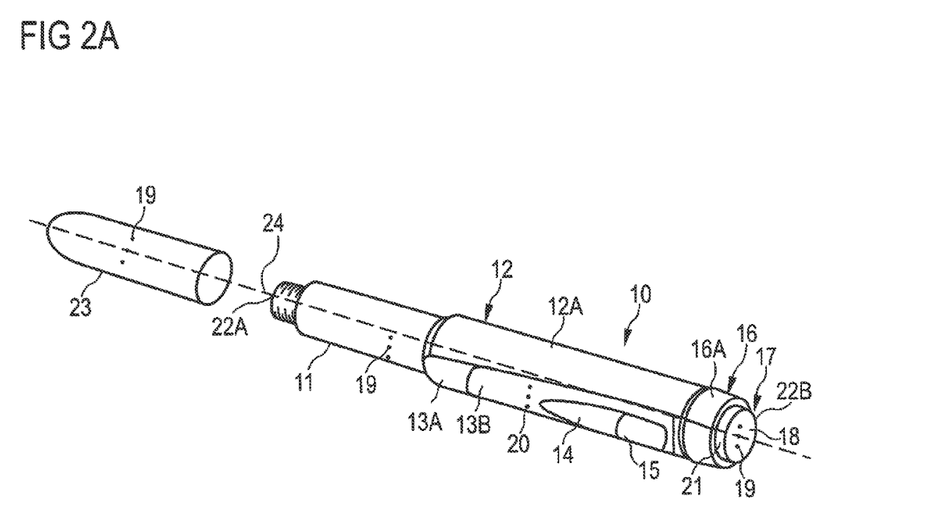
Figure 2B:
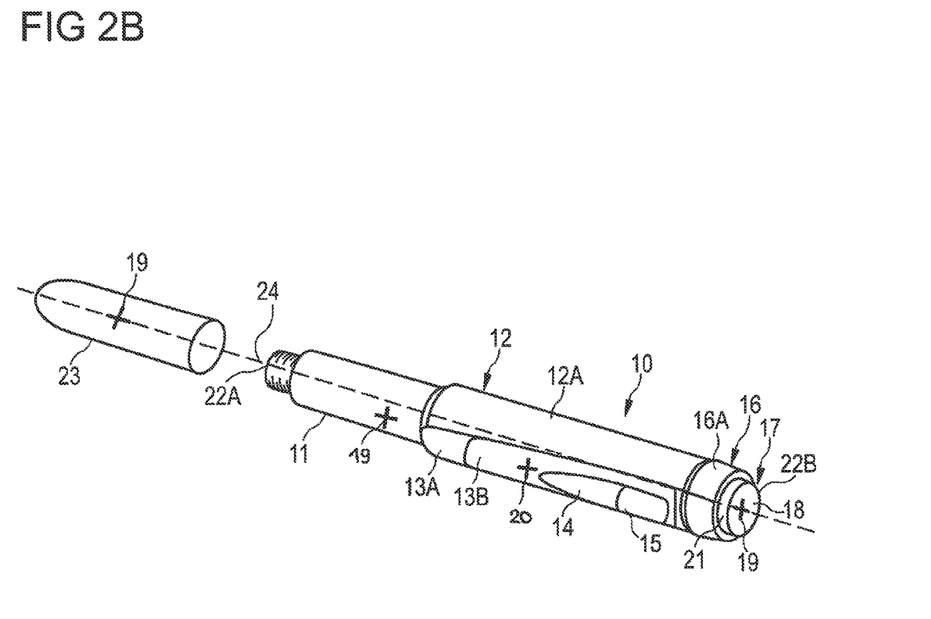
Figure 2C:
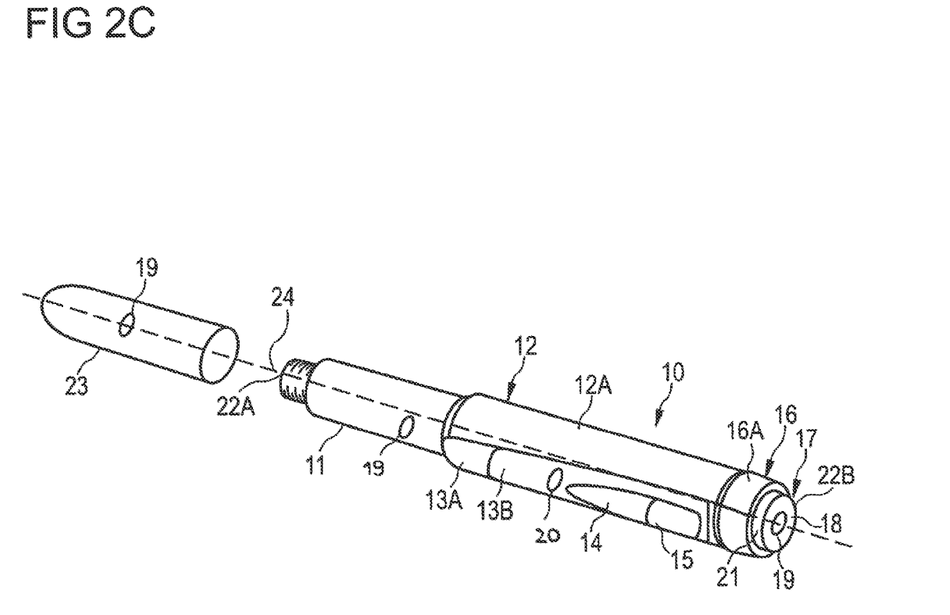

FIGS. 2A through 2C schematically show a set of three differently marked drug delivery devices. The device 10 shown in FIG. 2A is similar to the device 10 shown in FIG. 1.

The component marking 19 and the device marking 20 may help to distinguish different devices 10 holding different drugs from each other. These drug delivery devices 10 may comprise a similar exterior shape as shown in FIGS. 2A through 2C. The drug delivery devices 10 may comprise similarly shaped exchangeable components and a similarly shaped housing body 13A as described previously. In particular, the respective device 10 may comprise the previously described cap 23, the cartridge 25, the cartridge holder 11, the dose button 17 and the housing insert 13B which are, preferably releasably, connectable to the main housing 13A. Furthermore, the drug delivery devices 10 may comprise a similar colour.

The different drug delivery devices 10 may be adapted to hold different drugs. Due to the similar exterior shape and/or colour, a user may easily mix-up between the different drug delivery devices 10, in particular drug delivery devices 10 holding different drugs. This may have lethal or even fatal consequences for the user.

However, the exchangeable components of the respective device 10, in particular the cap 23, the cartridge 25, the cartridge holder 11, the dose button 17, the housing insert 13B and/or the label 14, may comprise component markings 19 and device markings 20 which are different from the markings 19, 20 of any other device 10 of the set of devices 10. In particular, the markings 19, 20 may be different for different drugs held in the cartridge 25 of the respective device 10.

The respective marking 19, 20 may comprise three insular bumps arranged in a line, as shown in FIG. 2A, for identifying a first particular drug held in a first device. The respective marking 19, 20 may comprise a cross-like marking, as shown in FIG. 2B, for identifying a second particular drug held in a second device. The respective marking 19, 20 may comprise a circular marking, as shown in FIG. 2C, for identifying a third particular drug held in a third device. In addition to these tactile markings, the respective marking 19, 20 may comprise a colour, a text marking and/or any marking as described in connection with the embodiment of FIG. 1.

Accordingly, by means of the component marking 19 and the device marking 20, the user may easily distinguish between the different drugs and, hence, between the different drug delivery devices 10. In particular, upon viewing and/or contacting the markings 19, 20 arranged on each of said devices 10, the user may realize immediately which device 10 he is operating and, in particular, which drug is held in the cartridge 25 of the respective device 10.

A table may be provided to the user to link the respective marking 19, 20 to the drug held in the respective device 10. Especially for blind users, a Braille link to the drug name may be provided in the table, so that the user may learn which marking 19, 20, in particular which tactile marking 19, 20, identifies which drug.

Furthermore, a case for at least one device 10 or a plurality of devices 10 may be provided (not explicitly shown). The case may be a carry case. The case may be adapted and arranged to receive the respective device 10 in an interior of the case. The case may be made of a robust and water-repellent material. Preferably, the case is closable. The case may provide additional protection for the respective drug delivery device 10 from environmental influences, from vibrations or other effects which may damage the device 10.

Additionally or alternatively, a drug packaging for the drug held in the device 10 may be provided (not explicitly shown). The drug packaging may be adapted to retain the drug, in particular a cartridge holding the drug, for the device 10, for example. The drug packaging may be retained in the case, for example. In particular, the drug packaging may be retained in the case together with the device 10. Accordingly, additional drug may be supplied in the case in addition to the drug contained in the device 10, e.g. by means of a replacement cartridge containing the drug.

A marking, e.g. a storage marking, may be provided on an outer surface of the case and/or of the drug packaging. The storage marking may comprise a tactile, colour, text and/or symbol marking This storage marking may provide the same information to the user, in particular information about the drug held in the device 10, as the device marking 20 and the component marking 19. In particular, the respective storage marking may be substantially equivalent or identical to the markings 19, 20. Accordingly, even during storage of the device 10, the user can identify the drug held in the device 10 by viewing and/or contacting the storage marking provided on the case and/or the drug packaging.

Figure 3A:
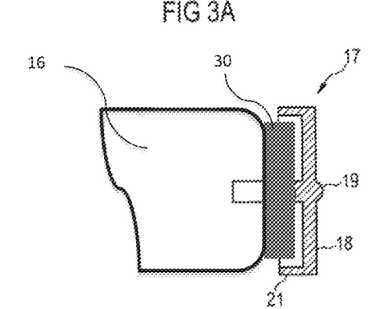
Figure 3B:
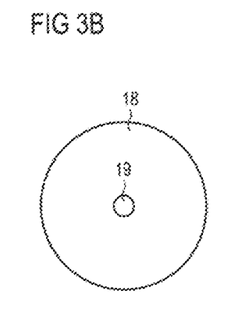
Figure 3C:
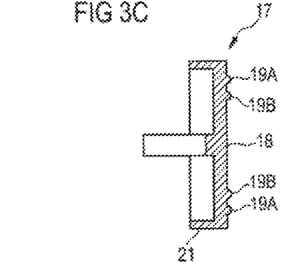
Figure 3D:
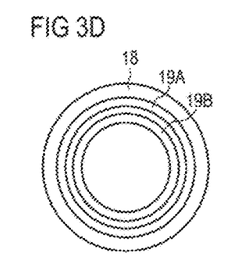
Figure 3E:
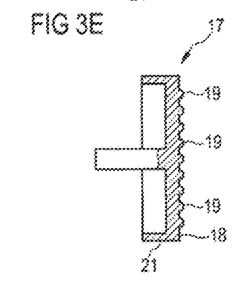
Figure 3F:
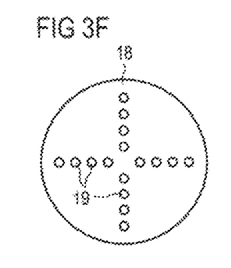

FIGS. 3A through 3F schematically show exemplary embodiments of a part of the drug delivery device of FIG. 1. The pairs comprising FIGS. 3A, 3B and the ones comprising FIGS. 3C, 3D as well as the ones comprising FIGS. 3E, 3F illustrate the same dose button embodiment on the basis of a sectional view (FIGS. 3A, 3C and 3E) and of a plan view (FIGS. 3B, 3D and 3F).

The dose button 17 comprises the previously mentioned actuation surface 18. The actuation surface 18 is provided with a component marking 19. The dose button 17 comprises a side face 21. The side face 21 is not contacted by the user for setting and delivering the dose.

In FIG. 3A the component marking 19 comprises one insular knob arranged in the middle of the actuation surface 18. The said component marking 19 identifies one particular type of drug, e.g. short-acting insulin. The knob comprises a rounded surface to prevent the user from being hurt while contacting the actuation surface 18. FIG. 3B shows a top view of the dose button 17 shown in FIG. 3A.

In FIG. 3C the component marking 19 comprises two annular shaped and concentrically arranged protrusions 19A, 19B arranged on the actuation surface 18. A plane surface is provided between the protrusions 19A, 19B. Said component marking 19A, 19B identifies an other particular type of drug, e.g. long-acting insulin. FIG. 3D shows a top view of the dose button 17 shown in FIG. 3C.

In FIG. 3E the component marking 19 comprises a plurality of insular knobs. The knobs are distributed over the actuation surface 18. The knobs are grouped in lines. The lines form a cross-like structure. Apart from these knobs the actuation surface 18 is plane. As indicated in FIG. 3F, the knobs form a vertical and horizontal line. Said lines cross at the middle of the actuation surface 18 of the dose button 17.

The above described structures of the component marking 19 of course apply for the device marking 20, as well.

Other implementations are within the scope of the following claims. Elements of different implementations may be combined to form implementations not specifically described herein.

The invention claimed is:

1. A drug injection device comprising:
a main housing comprising a tubular shape provided with at least one tactile device marking,
a housing body, which is part of the main housing,
a drive mechanism arranged at least partly within with the main housing, the drive mechanism comprising a dose dial element and a dose button having a proximal end face, wherein the dose dial element is rotatable relative to the main housing and the dose button,
a cartridge holding one or a plurality of doses of a drug, and
a cartridge holder configured to retain the cartridge,
wherein the dose button is axially displaceable with respect to the main housing and has an actuation surface that is part of the proximal end face,
wherein the cartridge or the cartridge holder is provided with at least one tactile component marking,
wherein the actuation surface has a further tactile component marking, and
wherein the at least one tactile device marking, the further tactile component marking, and the at least one tactile component marking are identical and identify the drug.

2. The drug injection device according to claim 1, wherein the cartridge holder is screwed to the main housing.

3. The drug injection device according to claim 1, wherein the at least one tactile device marking, the further tactile component marking, and the at least one tactile component marking are formed unitarily through being milled lathed, or moulded into an outer surface of the main housing, the actuation surface, and the cartridge or cartridge holder.

4. The drug injection device according to claim 1, wherein the main housing comprises a housing insert which is releasably connected to the main housing, wherein the at least one tactile device marking is provided on the housing insert.

5. The drug injection device according to claim 1, wherein the at least one tactile device marking and the at least one tactile component marking each comprise at least one colour marking.

6. The drug injection device according to claim 1, wherein the at least one tactile device marking and the at least one tactile component marking each comprise at least one text marking.

7. The drug injection device according to claim 6, wherein the at least one text marking comprises a name of the drug for the drug delivery device.

8. The drug injection device according to claim 1, wherein the at least one tactile device marking and the at least one tactile component marking each comprise at least one symbol.

9. A set of drug injection devices comprising at least two drug injection devices, the at least two drug injection devices comprising:
a first injection device comprising the injection device of claim 1, and
a second injection device comprising:
a main housing comprising a tubular shape provided with at least one tactile device marking,
a housing body, which is part of the main housing of the second injection device,
a drive mechanism arranged at least partly within with the main housing of the second injection device, the drive mechanism of the second injection device comprising a dose dial element and a dose button having a proximal end face, wherein the dose dial element of the second injection device is rotatable relative to the main housing of the second injection device and the dose button of the second injection device,
a cartridge holding one or a plurality of doses of a drug, and
a cartridge holder configured to retain the cartridge of the second injection device,
wherein the dose button is axially displaceable with respect to the main housing of the second injection device and has an actuation surface that is part of the proximal end face of the dose button of the second injection device,
wherein the cartridge or the cartridge holder of the second injection device is provided with at least one tactile component marking,
wherein the actuation surface of the dose button of the second injection device has a further tactile component marking, and
wherein the at least one tactile device marking, the further tactile component marking, and the at least one tactile component marking of the second injection device are identical and identify the drug,
wherein the at least one tactile device marking, the further tactile component marking, and the at least one tactile component marking of the second injection device differ from the at least one tactile device marking, the further tactile component marking, and at least one tactile component marking of the first injection device, and
wherein the drug held by the first injection device differs from the drug held by the second injection device.

10. The set of drug injection devices according to claim 9, wherein:
the at least one tactile device marking, the at least one tactile component marking, and the at least one further tactile component marking of the first injection device further comprise at least one of at least one colour marking, at least one text marking, or at least one symbol marking, and
the at least one tactile device marking, the further tactile component marking, and the at least one tactile component marking of the second injection device further comprise at least one of at least one colour marking, at least one text marking, or at least one symbol marking.

11. The set of drug injection devices according to claim 9, wherein the set of drug injection devices are disposable.

12. The set of drug injection devices according to claim 9, wherein the set of drug injection devices are re-usable.

13. A set of drug injection devices comprising at least two drug injection devices, the at least two drug injection devices comprising:
a first injection device comprising the injection device according to claim 1, and
a second injection device comprising:
a main housing comprising a tubular shape provided with at least one tactile device marking,
a housing body, which is part of the main housing of the second injection device,
a drive mechanism arranged at least partly within with the main housing of the second injection device, the drive mechanism of the second injection device comprising a dose dial element and a dose button having a proximal end face, wherein the dose dial element of the second injection device is rotatable relative to the main housing of the second injection device and the dose button of the second injection device,
a cartridge holding one or a plurality of doses of a drug, and
a cartridge holder configured to retain the cartridge of the second injection device,
wherein the dose button is axially displaceable with respect to the main housing of the second injection device and has an actuation surface that is part of the proximal end face of the dose button of the second injection device,
wherein the cartridge or the cartridge holder of the second injection device is provided with at least one tactile component marking,
wherein the actuation surface of the dose button of the second injection device has a further tactile component marking, and
wherein the at least one tactile device marking, the further tactile component marking, and the at least one tactile component marking of the second injection device are identical and identify the drug,
wherein the at least one tactile device marking, the further tactile component marking, and the at least one tactile component marking of the second injection device are identical to the at least one tactile device marking, the further tactile component marking, and the at least one tactile component marking of the first injection device, and
wherein the drug held by the first injection device is identical to the drug held by the second injection device.

14. The set of drug injection devices according to claim 13, wherein the first drug injection device of the set of drug injection devices is disposable and the second drug injection device of the set of drug injection devices is reusable.

* * * * *

UNITED STATES PATENT AND TRADEMARK OFFICE
CERTIFICATE OF CORRECTION

PATENT NO. : 10,207,056 B2
APPLICATION NO. : 13/582561
DATED : February 19, 2019
INVENTOR(S) : Richard James Vincent Avery et al.

Page 1 of 1

It is certified that error appears in the above-identified patent and that said Letters Patent is hereby corrected as shown below:

In the Claims

In Column 18, Line 65, Claim 3, delete "milled" and insert -- milled, --

Signed and Sealed this
Sixteenth Day of July, 2019

Andrei Iancu
*Director of the United States Patent and Trademark Office*